United States Patent [19]

Janata et al.

[11] 4,397,714
[45] Aug. 9, 1983

[54] SYSTEM FOR MEASURING THE CONCENTRATION OF CHEMICAL SUBSTANCES

[75] Inventors: Jiri Janata, Salt Lake City; Robert J. Huber, Bountiful; Rosemary L. Smith, Salt Lake City, all of Utah

[73] Assignee: University of Utah, Salt Lake City, Utah

[21] Appl. No.: 159,994

[22] Filed: Jun. 16, 1980

[51] Int. Cl.³ ............................................. G01N 27/26
[52] U.S. Cl. ................................... 204/1 T; 204/84; 204/406; 357/25; 357/23
[58] Field of Search ........... 357/25, 23, 23 R, 23 MG, 357/84; 73/61 R; 204/1 T, 195 M, 195 R

[56] References Cited

U.S. PATENT DOCUMENTS

| 4,020,830 | 5/1977 | Johnson et al. | 357/25 |
| 4,180,771 | 12/1979 | Guckel | 357/25 |
| 4,218,298 | 8/1980 | Shimada et al. | 357/25 |
| 4,238,757 | 12/1980 | Schenck | 357/25 |

FOREIGN PATENT DOCUMENTS 52-24085  2/1977  Japan .................................... 357/25

OTHER PUBLICATIONS

Barthold, IBM Tech. Discl. Bulletin, vol. 19, No. 4, Sep. 1976, p. 1292.

Primary Examiner—William D. Larkins
Attorney, Agent, or Firm—Thorpe, North & Western

[57] ABSTRACT

A solid state chemically sensitive integrated circuit includes three field-effect transistors (FETs) fabricated on a single semiconductor substrate. The gate of a first FET is overlaid with a chemically sensitive element that is adapted to create an electrochemical potential at the gate when exposed to selected chemical substances. This gate is also electrically connected to the source of a second FET and the drain of a third FET. The second and third FETs are used as switches to selectively connect the gate of the first FET to ground, to an external reference potential, or to isolate it from all external signals. In the latter case, only the interaction between the chemically sensitive element and external chemical substances may affect the first FET's operation thus allowing the first FET, when so isolated, to provide a measure of the chemical properties of the substance to which its chemically sensitive element is exposed. The presence of the second and third FETs allows the first FET to be protected from static shock during routine handling and when the device is not in use. They also allow the performance of the first FET to be fully characterized by permitting a controlled gate voltage to be applied to the first FET.

17 Claims, 7 Drawing Figures

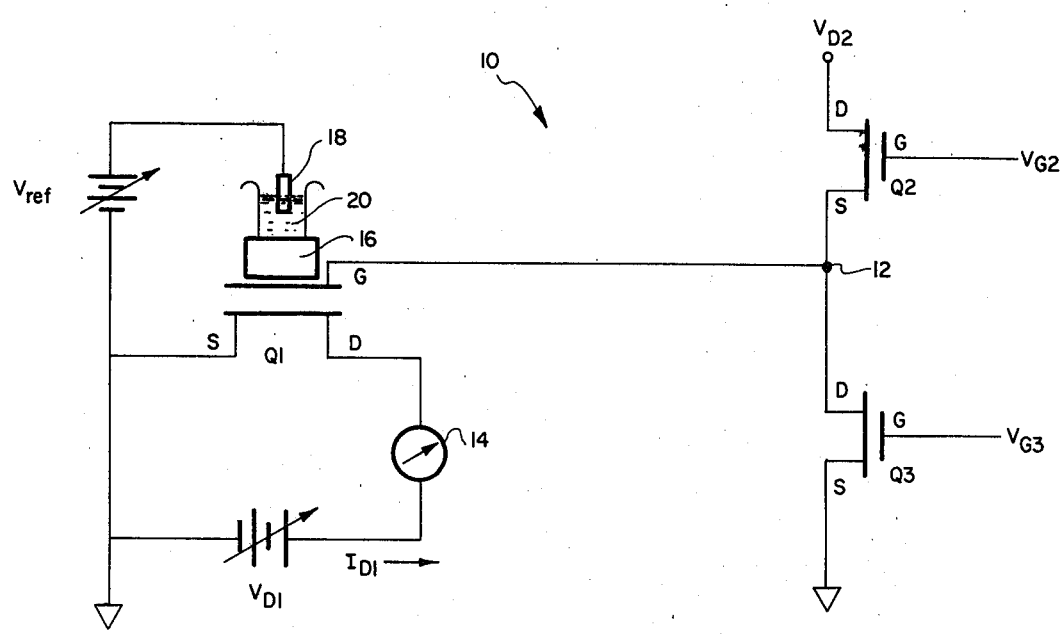
Fig. 1
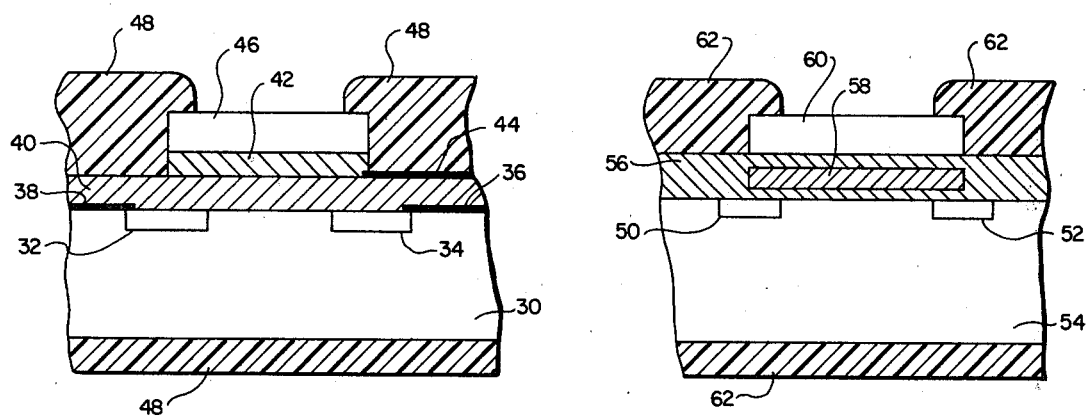
Fig. 2                    Fig. 3

SYSTEM FOR MEASURING THE CONCENTRATION OF CHEMICAL SUBSTANCES

BACKGROUND OF THE INVENTION

This invention relates to a system for selective detection of chemical substances and measurement of the concentration thereof; and more particularly to a field-effect integrated circuit adapted for detecting and measuring chemical substances, and to a method of using such an integrated circuit (or descrete equivalent thereof) for chemical measurements.

The chemical sensitive field-effect transistor (FET) has, in recent years, provided a valuable technique for measuring and detecting selected chemical properties. The basic chemical sensitive FET, or CHEMFET as it has come to be known (or ISFET—ion sensitive FET), was first disclosed in U.S. Pat. No. 4,020,830 (1977). This basic CHEMFET consists primarily of a semiconductor substrate in which a pair of spaced-apart diffusion regions are placed at an upper surface thereof. A chemical sensitive medium or layer is placed over these spaced-apart diffusion regions and the surface area lying therebetween (known as the gate area), often with an insulating layer between this medium and the surface of the substrate. As the chemical sensitive medium or layer is exposed to chemical substances, a voltage potential (hereinafter referred to as an electrochemical potential for purposes of this application) induces or enhances a conductive channel between the spaced-apart diffusion regions. Thus, when such an electrochemical potential is present, current may flow from one diffusion region through the enhanced channel to the other diffused region. Where spaced-apart regions are used in this manner, the FET is referred to as an "enhancement mode" FET because it will not allow current to flow therethrough unless a voltage is present over the region lying between the diffusion regions.

Another type of FET is the "depletion mode" FET, in which current is allowed to flow between the diffusion regions when no voltage is present over the gate area. The amount of current that flows through the channel is controlled by a voltage which "depletes" the width thereof in a manner that is well known in the art so as to eventually "pinch off" the channel when a potential of a certain value is reached. Depletion mode devices may also be used for CHEMFET applications whenever the electrochemical potential is the potential used to "deplete" the width of the conductive channel.

The initial disclosure of the CHEMFET device in U.S. Pat. No. 4,020,830 has been followed by other publications. See, e.g., P. W. Cheung, D. G. Fleming, W. H. Ko, and M. R. Neuman (editors), "Theory, Design, and Biomedical Applications of Solid State Chemical Sensors", CRC Press, West Palm Beach, Florida (1978), and especially an article therein entitled "Ion-Sensitive Implantable Electrodes Fabricated by Hybrid Technology" by S. S. Yee and M. A. Afromowitz, pp. 81–87. Also see U.S. Pat. No. 4,133,735 which discloses a type of hybrid ion-sensitive electrode in which the ion-sensitive structure is physically separated from the FET.

One of the problems of CHEMFET (or ISFET) devices is an inherent inability to be fully characterized as far as performance characteristics are concerned. That is, heretofore, the only way to apply a potential to the "gate" of the CHEMFET device, thereby enabling the CHEMFET to operate, was to apply an electrochemical voltage thereto. This meant exposing the CHEMFET device to a chemical substance or solution. However, by so doing, it is difficult to separate the chemical effects from the other performance characteristics of the device. For example, the CHEMFET device can be temperature and light dependent; yet it is difficult to separate those variations in the CHEMFET device performance that are attributable to light and temperature changes versus those that are attributable to changes in the chemical properties of the substance to which the device is exposed. Thus, generally speaking, the prior art CHEMFET devices must be used in a highly controlled environment, one in which temperature is held very constant, and where light is either blocked out or is also held at a very constant level. Furthermore, it has not been possible to use the CHEMFET device to characterize the performance of particular chemical sensitive membranes or layers that are used therewith. Whereas, if the complete voltage-current characteristics of a given CHEMFET device were known, then it would be possible to insert thereon a particular chemical sensitive membrane or layer that was to be evaluated, measure the current that flows through the device, and from such a measurement accurately predict how much of an electrochemical voltage the particular chemically sensitive membrane or layer must have produced to allow the measured current to flow.

Another problem with prior art CHEMFET or (ISFET) devices is their high susceptability to damage during manufacture or routine handling due to electrostatic charges.

Still another problem of the prior art CHEMFET (or ISFET) devices is that the chemical sensitive layer or membrane used with the device can be easily contaminated or be incompatable with the semiconductor substrate and diffusion regions. Thus, the materials for the chemically sensitive membrane or layer and the semiconductor materials of the FET device must be carefully selected. This results in a severe limitation as to the range of materials to which the CHEMFET device may be sensitized.

A further problem associated with the prior art enhancement mode CHEMFET devices is that it is not possible to operate them without exposing them to a chemical substance (thereby generating an electrochemical gate voltage that enhances a channel through which current may flow). Thus, these devices cannot be "burned-in", or stabilized, as is common practice with semiconductor devices, unless such a "burn-in" is performed while exposing the chemical sensitive layer to a chemical substance, which exposure is not practical over a long period of time.

SUMMARY OF THE INVENTION

A primary object of the present invention is to provide a greatly improved chemical sensitive system or device for selectively detecting and measuring the chemical concentration of substances to which it is exposed.

Another object of the invention is to provide such an improved system wherein the electrical parameters thereof may be determined accurately and independently of any chemical effects.

A further object of the invention is to provide, in one embodiment thereof, such a system in a single FET integrated circuit.

An additional object of the invention is to provide such a single chemically sensitive integrated circuit that is protected from the deleterious effects of static electric charge during manufacturing and routine handling.

It is also an object of the invention to provide an improved chemical sensitive system that permits a great deal of freedom in choosing the material of the chemical sensitive portion thereof by minimizing material compatibility problems, thereby providing a wide range of chemical substances to which the system may be adapted for detection and measurement purposes.

It is still a further object of the invention to provide such a system wherein temperature and light variations of the system may be measured independently of the chemical sensitive effects.

A further object is to provide a system that may be shielded from the effects of light.

Still another object of the invention is to provide a system that may be "burned-in" over extended periods of time without the need of exposing the system to a chemical substance, thereby allowing its performance parameters to be stabilized.

The above and other objects of the present invention are realized in a specific illustrative circuit configuration that employs a field-effect transistor, a reference voltage source, and a reference electrode. The field-effect transistor includes a semiconductor substrate with two spaced-apart diffusion regions located at the surface of the substrate, an insulator layer overlying the substrate, a conductive gate layer overlying the insulator layer above the diffusion regions and gate region therebetween, and a chemical sensitive layer overlying the conductive gate layer. The reference electrode coupled through the reference potential source is used in conjunction with the transistor in the standard CHEM-FET arrangement. However, the employment of the conductive gate layer ensures uniformity of the developed potential along the lower surface of the chemical sensitive layer, and improves response time.

In one embodiment of the invention, first and second switching elements are coupled to the conductive gate layer of the field-effect transistor. The first switching element enables selective coupling of the gate layer to a voltage source, whereas the second switching element enables coupling the gate layer to ground potential. Connecting the gate layer to ground serves to protect the field-effect transistor from static electric charge damage during manufacture and routine handling. Connecting the gate layer to a voltage source allows the performance of the field-effect transistor (such as vis a vis light and temperature variations) to be thoroughly characterized independent of chemical effects. Finally, if the gate layer is connected neither to the voltage source nor ground potential (i.e., it is electrically isolated), then the gate layer will assume a potential determined by the combined effects of the reference electrode, the chemically sensitive layer, and the substance to which the device is exposed. In other words, the field-effect transistor will function similar to a traditional CHEMFET device.

Several different embodiments of the gate structure of the chemically sensitive Q1 may be employed with the invention. These alternative embodiments are fully described in the following drawings and detailed disclosure.

BRIEF DESCRIPTION OF THE DRAWINGS

The above and other objects, features and advantages of the invention will become apparent from the following more particular description presented in connection with the accompanying drawings, in which:

FIG. 1 is a schematic electrical diagram of a system for measuring chemical properties of a substance in accordance with the principles of the present invention;

FIG. 2 is a cross-section view of one embodiment of the chemical sensitive FET Q1 of FIG. 1;

FIG. 3 is a cross-sectional view of an alternative embodiment of Q1;

DESCRIPTION OF THE PREFERRED EMBODIMENTS

Figure 4:
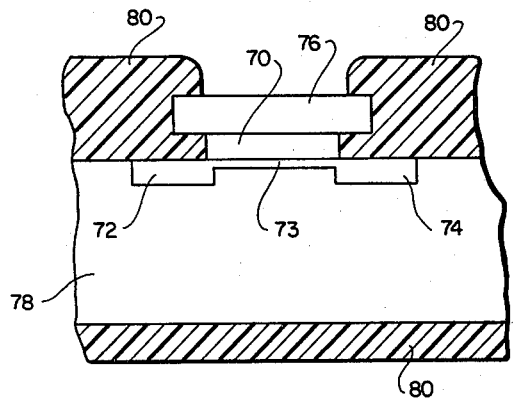
FIG. 4 is a cross-sectional view of another alternative embodiment of Q1.

Referring now to FIG. 1, there is shown a schematic diagram representation of a system for measuring the concentration of chemical substances. The system includes three transistors, identified as Q1, Q2 and Q3. Each of these transistors is adapted to allow a current to flow from an input port to an output port as a function of a control signal applied at a control port thereof. In the preferred embodiment of the invention, Q1, Q2 and Q3 are field-effect transistors (FETs), having source, drain, and gate terminals. The source terminals of the transistors of FIG. 1 are identified by an "S"; the drain terminals by a "D"; and the gate terminals by a "G". The three transistors may be of any suitable type, such as a metal-insulator-semiconductor FET (MISFET or MOSFET), a junction FET, or a Schottky gate FET. Transistor Q2 is ideally an enhancement mode device described earlier. Transistor Q3, on the other hand, is ideally a depletion mode device, also described earlier. Transistor Q1 may be either an enhancement or depletion mode device, depending on the requirements of a particular application.

As shown in FIG. 1, the gate terminal of Q1 is connected to a common tie point 12 to which the source terminal of Q2 and the drain terminal of Q3 are also connected. The drain terminal of Q2 is connected to an external reference potential, identified as $V_{D2}$ in FIG. 1. The source terminal of the transistor Q3 is tied to ground. The gate voltages of both Q2 and Q3 may be supplied by appropriate control voltage sources $V_{G2}$ and $V_{G3}$ respectively.

A reference potential $V_{D1}$ is applied between the source and drain terminals of the transistor Q1. An ammeter 14, or other current measuring device, is inserted in series with the potential between the drain source terminals of transistor Q1. The source terminal of Q1, as well as one side of the external potential $V_{D1}$, are also grounded.

A chemical sensitive layer, membrane, or medium 16 is deposited over the gate region of transistor Q1. This chemical sensitive layer 16 is used in connection with a reference electrode 18 and an external reference potential $V_{REF}$, to generate an electrochemical voltage at the gate of Q1 as a function of the chemical properties and concentration of a substance 20 to which the layer 16 is exposed.

In operation, the FETs Q2 and Q3 are used as switches to control the external gate voltage, if any, that is allowed to be applied to the gate of FET Q1. When there are no external voltages applied to the gates of Q2 and Q3, then Q3 will be "on" and Q2 will be "off". This means that the gate of Q1 will be grounded through the "on" drain-source channel of Q3. With the gate of Q1 grounded in this fashion, Q1 is protected from damage that might otherwise occur due to electrostatic charge build-up.

To measure the performance characteristics of the transistor Q1, the gate voltage $V_{G3}$ of Q3 is increased to a value sufficient to pinch off its drain source channel thereby turning Q3 "off", and an appropriate gate voltage $V_{G2}$ is concurrently applied to the gate of Q2 to "enhance" a channel therein, thereby turning Q2 "on". With Q2 "on", and Q3 "off", the gate of Q1 is tied to the reference voltage $V_{D2}$. $V_{D2}$ may then be used as the gate voltage of Q1, and the performance characteristics of Q1 may be measured as they would be for any conventional FET. Note that in this mode of operation (that is with the gate Q1 tied to an external reference potential $V_{D2}$), the electrochemical voltage, if any, that would otherwise be present at the gate of Q1 is shorted through Q2 to the reference potential $V_{D2}$. Thus, any chemical effects are blocked out, and only the performance characteristics of Q1, i.e., those not attributable to the chemical interaction of the substance 20 with the chemical sensitive layer 16, may be measured.

To measure the chemical properties of the substance 20, appropriate gate voltages $V_{G2}$ and $G_{G3}$ are applied so that both Q2 and Q3 are "off", to thereby isolate the tie point 12 and allow Q1 to function similar to a conventional CHEMFET. The operation of the CHEMFET has been fully disclosed in U.S. Pat. No. 4,020,830, which disclosure is hereby incorporated in this application by reference. In brief, when Q1 is to operate as a CHEMFET, the ions, antigens, enzymes, antibodies, and the like of the substance 20 are allowed to interact with the chemical sensitive layer 16 so as to generate an electrochemical potential that will appear at the gate of Q1. This electrochemical potential serves to enhance the conductive path between the drain and source terminals of Q1 as would any gate voltage that is applied thereto. However, because this voltage is a function of the chemical properties of the substance 20, a measure of the drain current of Q1, labled $I_{D1}$ in FIG. 1, provides a convenient measure of the desired chemical properties and concentration of the substance 20.

Referring now to FIG. 2, there is shown a cross-sectional view of one embodiment of the chemical sensitive transistor Q1 of FIG. 1. The structure consists of a substrate material 30 having a pair of spaced-apart diffusion regions 32 and 34 located at an upper surface thereof. The substrate 30 has a desired doping polarity (such as p-doped) and the diffusion regions 32 and 34 have an opposite doping polarity (such as n-doped). A layer of electrical insulator material 40 is deposited or grown by oxidation over the surface of the substrate 30. This insulating material 40 may be any of the materials commonly used in FET technology such as silicon dioxide or a sandwich structure of silicon dioxide and silicon nitride.

A conductive track or channel 36 is formed in insulating material 40 so as to come in contact with the diffusion region 34. This conductive track 36 allows external electrical contact to be made with the diffusion region 34, which diffusion region serves as the drain of the transistor Q1. Similarly, a conductive track 38 is formed in the insulating material 40 so as to come in contact with the diffusion region 32, which diffusion region serves as the source terminal of Q1. Note, as thus structured, the source and drain are essentially symetrical, and generally it is not significant which region is considered as the source and which is considered as the drain.

A conductive gate material 42 is deposited over the insulator material 40 so as to overlie that portion of the substrate surface lying between the diffusion regions 32 and 34. Any suitable conductive material may be used for this layer such as aluminum, gold, silver, molybdenum, tungsten, conductive polycrystalline silicon, or platinum. Electrical contact is made with this conductive layer 42 by means of another conductive track or channel 44 that, in the configuration shown in FIG. 2, is deposited on top of the layer of insulating material 40.

A chemical sensitive layer or membrane 46 is placed over the gate material 42 so as to be in direct contact therewith. This chemical sensitive layer 46 could be, but is not limited to, any of the types disclosed in U.S. Pat. application Ser. No. 4,020,830. With the chemical sensitive layer 46 in direct contact with the conductive gate layer 42, the gate conductor will thus assume the potential determined by the bottom of the chemical sensitive layer 46. This potential is referred to as the electrochemical potential for purposes of this application. A particular advantage of the structure shown in FIG. 2 is that the gate conductor 42 is at an equipotential, meaning that the potential is everywhere equal along its surface. This means that the transistor Q1 can be accurately described by all of the existing theory developed for the MOSFET (or MISFET or IGFET). Note, that if the gate conductor 42 were not present, then the structure would be the same as the CHEMFET devices previously disclosed in U.S. Pat. No. 4,020,830 and other literature. Such traditional CHEMFET devices do not necessarily have an equipotential along the lower surface of the chemically sensitive layer 46, and therefore do not behave according to the existing theory developed for MOSFETs. The addition of the conductive layer 42, therefore, advantageously allows existing MOSFET theory to be applicable to the new chemically sensitive FET structure shown in FIG. 2. Moreover, it has been experimentally determined that the addition of the gate conductor 42 improves the speed of response of the device by eliminating the need for lateral movement of chemical species in the chemically sensitive layer 46. There are, of course, several applications of CHEMFETs (or ion sensitive FETs) where the electrical time response can be critically important, such as a multisensor operation where a multiplexing of bias voltage may be necessary.

Still referring to FIG. 2, a substance impervious material 48 is deposited about the substrate material 30, electrical insulator material 40, conductive gate material 42 and chemical sensitive layer 46, exposing only that portion of the layer 46 that is to come in contact with the chemical substance to be measured. The substance impervious material 48 thus serves as a protective shield around the device so that only desired portions of the chemical sensitive layer 46 come in contact with external substances. Note also from the structure of FIG. 2, that the conductive gate layer 42 serves as an additional shield to prevent the chemical sensitive layer 46 from coming in direct contact with the insulating gate material 40. This can be important in some applications because of the incompatibility of the chemical sensitive layer 46 with many insulating materials. Thus, the structure of FIG. 2 allows the freedom of choosing the chemical sensitive layer 46 from any materials that need only be compatible with the conductive gate layer 42. The conductive gate layer 42 advantageously is also an opaque material, thus allowing the layer 42 to serve the additional function of a light shield, thereby protecting the sensitive gate region of the device from the undesirable exposure to ambient light.

Referring now to FIG. 3 there is shown a cross-sectional view of alternative embodiment of the chemical sensitive FET Q1 of FIG. 1. The structure of FIG. 3 is substantially the same as that shown in FIG. 2, except that a conductive gate material 58 is embedded within (rather than overlying) an electrical insulator material 56. The conductive gate material 58 is positioned so as to be above the region of a substrate 54 that lies between diffusion regions 50 and 52. A chemical sensitive layer 60 is placed above the insulating layer 56 so as to be directly above, but not in contact with, the conductive gate layer 58. Suitable conductive tracks, not shown, are used in a manner similar to that shown in FIG. 2, to make electrical contact, where needed, with the diffusion regions 50 and 52, and the gate 58. A substance impervious material 62 is deposited about the structure so as to protect all but a desired portion of the chemical sensitive layer 60 from the substance to which the structure is exposed.

Note in FIG. 3 that the insulator layer 56, in addition to insulating the gate conductor 58 from the diffusion regions 50 and 52, also covers the top of the gate conductor 58 and separates it from the chemical sensitive layer 60. This allows the gate conductor to be chosen from a wide range of materials.

In FIG. 4 there is shown a cross-sectional view of another alternative embodiment of the FET Q1 of FIG. 1. Here the FET Q1 is built with a Schottky barrier gate 70. In this structure, the two spaced-apart diffusion regions 72 and 74 are connected by a thin, high resistivity layer 73 of the same conductivity type as regions 72 and 74. This layer 73 provides a continuous conductive path for electric current to flow between the spaced-apart regions 72 and 74 unless interrupted by the effects of the Schottky barrier gate 70. Layer 73 can be fabricated by any appropriate means such as ion implantation. Note that in the structure of FIG. 4 there is no insulative layer between the conductive gate layer 70 and the high resistivity layer 73. The conductive material 70 is chosen from those materials which will form a Schottky barrier, also known in the semiconductor technology literature as a blocking contact, when in contact with a semiconductor. For example, if the layer 73 is high resistivity n-type silicons, two possible choices for the conductor 70 are aluminum or platinum.

When a voltage of the proper polarity and magnitude is applied between the conducting layer 70 and the substrate 80 in FIG. 4, the effects of the Schottky barrier between 70 and 73 will deplete the number of mobile, charge carriers in layer 73 thereby reducing the magnitude of any electric current flowing between the spaced-apart diffusion regions 72 and 74. A chemical sensitive layer 76 is in direct contact with the gate conductor 70. A substance impervious material 80 may be used as discussed previously to protect the entire structure, except for the desired portions of the chemical sensitive layer 76, from any substance to which the device may be exposed.

Changes in the electric potential between the chemical sensitive layer 76 and the chemical solutions to which it is exposed will be transmitted to the conducting layer 70. Any such change will effect the voltage between the conducting layer 70 and the substrate 80 when transistor Q1 is properly operated with a reference electrode as described previously. Such change in voltage between 70 and 80 will change the amount of electric current flowing between the spaced-apart diffusion regions 72 and 74 which can be measured to thereby measure the concentration of chemical species in the solution being tested.

Figure 5:
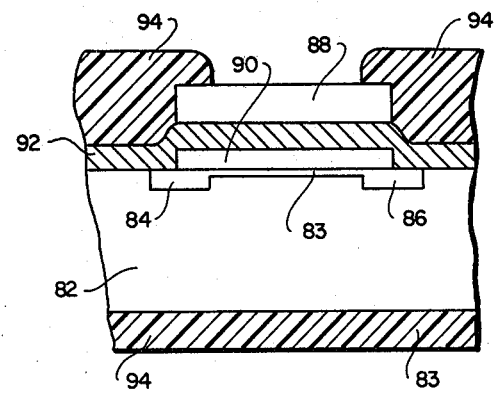
FIG. 5 is a cross-sectional view of still another alternative embodiment of Q1.

The structure shown in FIG. 5 is similar to that shown in FIG. 4 in that a Schottky barrier gate 90 is placed in direct contact with the upper surface of a substrate material 82 in which a pair of spaced-apart diffusion regions 84 and 86 have been placed. As in the case shown in FIG. 4, the spaced-apart diffusion regions 84 and 86 are connected by a thin, high resistivity layer 83 of the same conductivity type as regions 84 and 86. However, the gate 90 is insulated from the chemical sensitive layer 88 by an insulating layer 92. This structure allows many of the desirable performance characteristics of the blocking interface to be achieved, and offers the further advantage of permitting a wider range of materials to be used for the gate and the chemical sensitive layer. As with the other structures disclosed, a substance impervious material 94 may be placed around the device so as to isolate all but selected portions of it from any foreign substances.

Figure 6:
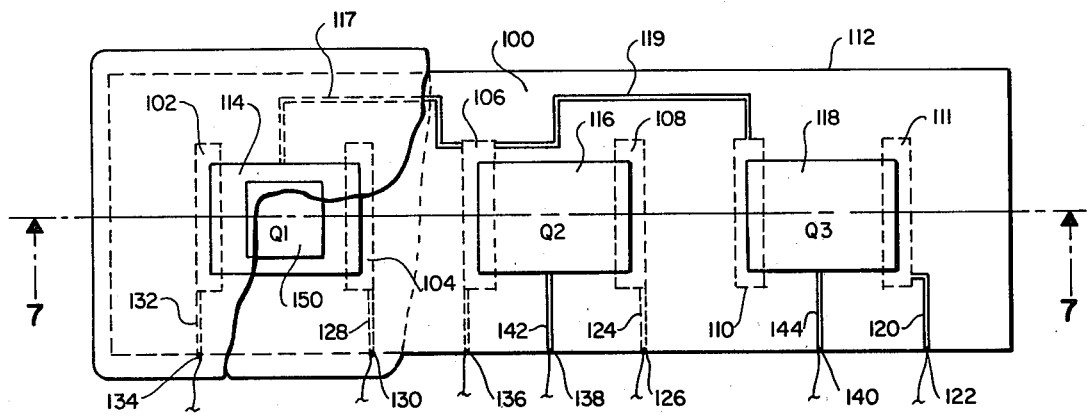
FIG. 6 is a top, partially cutaway view of an integrated circuit embodying the circuitry of FIG. 1.
Figure 7:
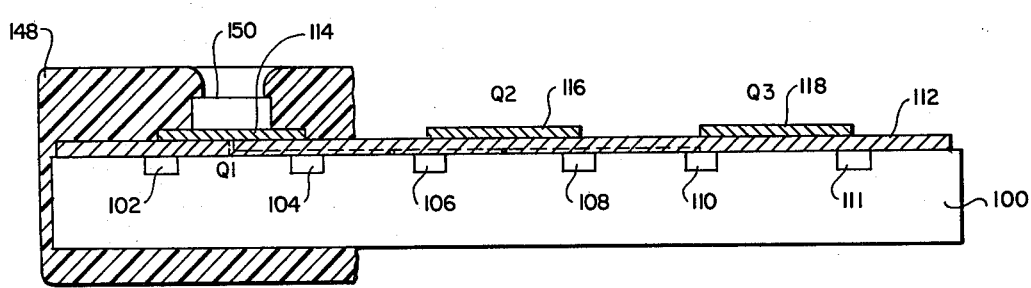
FIG. 7 is a cross-sectional view of the circuit of FIG. 6 taken along line 7—7.

Referring now to FIG. 6 there is shown a top view of an illustrative embodiment of the present invention incorporated into a single monolithic integrated circuit. The integrated circuit includes the three transistors Q1, Q2 and Q3 shown in FIG. 1. FIG. 7 is a cross-sectional view of FIG. 6 taken along the line 7—7 thereof, and hence the two figures will be referred to together in the following discussion.

The structure for Q1 shown in FIGS. 6 and 7 is the same as that shown in FIG. 2. However, it is to be understood that Q1 could be made according to any of the structures and methods disclosed in FIGS. 3, 4 or 5. Thus, the integrated circuit shown in FIGS. 6 and 7 includes a substrate material of a desired doping polarity into which diffusion regions of an opposite doping polarity have been placed at an upper surface thereof. A pair of spaced-apart diffusion regions 102 and 104 are associated with the transistor Q1; while another pair of spaced-apart diffusion regions 106 and 108 are associated with the transistor Q2. Another pair of spaced-apart diffusion regions 110 and 111 are associated with the depletion mode transistor Q3. A layer of insulating material 112 is deposited or grown across the entire surface of the substrate 100. A conductive gate layer 114 for the FET Q1 is placed above the insulating material so as to be directly above the region between the diffusion regions 102 and 104. Similarly a conductive gate layer 116 for FET Q2 is placed above the region between the diffusion regions 106 and 108; while another conductive gate layer 118 for FET Q3 is placed above the region between the diffusion regions 110 and 111 of FET Q3. A conductive channel or tract 117 is deposited on the upper surface of the substrate material 100, or on the upper surface of the insulating layer 112, or a combination of these two locations, in order to connect the Q1 gate 114 to the diffusion region 106 of Q2 (which diffusion region is the equivalent of the source for the Q2 FET). Similarly a conducting track or channel 119 connects the diffusion region 106 (the source of Q2) to one end of the diffused region 110 of FET Q3. The other diffused region 111 of the FET Q3 is connected through another electrical track or channel 120 to a suitable external tie point 122 to which a wire, or other electrical contact, may be bonded for external electrical connection. In a similar fashion the diffusion region 108 is electrically connected through a conductive tack 124 to a tie point 126. The diffusion region 104 of Q1 is tied via an electrical conductive track 128 to an external tie point 130. The diffusion region 102 of Q1 is tied through a conductive track 132 to an external tie point 134. Also, a tie point 136 is connected to the substrate 100 so that external electrical contact may be made therewith. Additional tie points 138 and 140 are connected through conductive tracks 142 and 144 to the gates 116 and 118 of transistors Q2 and Q3 respectively. A chemical sensitive layer 150 is placed over the gate 114 of Q1. A substance impervious material 148, such as an epoxy resin, may be placed around the entire substrate 100, insulating layer 112, gate regions 114, 116 and 118, as well as the chemical sensitive layer 150, so as to shield the entire integrated circuit, save selected portions of the chemically sensitive layer 150, from being exposed to any foreign substances.

It should be noted that while the transistors Q1, Q2 and Q3 in FIGS. 6 and 7 are shown as being located along a single line, this geometry is not critical. For example, Q3 could be positioned above or below the transistor Q2 as seen in a top view as is shown in FIG. 6. Alternatively, transistor Q1 could be placed between transistors Q2 or Q3; or any other desired arrangement of the transistors could be used.

Referring again to the circuit shown in FIG. 1, it should be noted that the gate of Q1 may be alternately connected to $V_{D2}$ and electrically isolated in a periodic fashion. The difference between the voltage $V_{D2}$ an the electrochemical potential determined by the chemical effects will thus be translated into a time varying change in the value of the source-drain current $I_{D1}$. This time varying change can be used to advantage in electronic circuitry to detect changes in $I_{D1}$. For example, if $V_{D2}$ is held at a constant potential different from the electrochemical potential of the gate of Q1, and Q3 is held "off" while Q2 is switched on and off at a uniform rate, the current $I_{D1}$ will have a periodic variation at the switching rate whose amplitude is a function of the difference between $V_{D2}$ and the electrochemical potential of the gate of Q1. This, then will provide an AC measurement of the chemical properties of the substances to which the device is exposed, which measurement minimizes many of the long-term drift problems associated with DC measurements.

While the invention herein disclosed has been described by means of specific embodiments and applications thereof, numerous modifications and variations could be made thereto by those skilled in the art without departing from the spirit and scope of the present invention. It is therefore to be understood that within the scope of the appended claims, the invention may be practiced otherwise than as specifically described herein.

What is claimed is:

1. In a transducer system for detecting chemical properties of substances and including a semiconductor substrate having a doping polarity, a pair of spaced-apart diffusion regions located at the surface of the substrate and having doping polarity opposite that of said substrate material, an electrical insulator material overlying at least a portion of said diffusion regions and the surface of the substrate lying between the diffusion regions, a chemical selective system including a chemical selective membrane disposed over at least a portion of said insulator material, and a reference electrode connected in circuit with said spaced apart diffusion regions through a potential source, the combination thereof with an electrical conductive material disposed between the substrate and diffusion regions and the chemical selective membrane so as to be located above at least a portion of the substrate which is between the diffusion regions, a first switch element coupled to the conductive material and operable to selectively connect the conductive material to a voltage source, and a second switch element coupled to the conductive material and operable to selectively connect the conductive material to a ground potential source.

2. Apparatus for measuring the concentration of chemical substances comprising:

a semiconductor substrate having a doping polarity;

a pair of spaced-apart diffusion regions located at the surface of said substrate material and having a doping polarity opposite that of the substrate material;

an electrical insulator material overlying at least a portion of said diffusion regions and the surface of the substrate material lying between the diffusion regions;

a conductive layer of material overlying at least a portion of said electrical insulator material;

a reference electrode coupled in circuit relationship with said diffusion regions through a reference potential source;

switch means for electrically connecting the conductive layer of material selectively to a voltage source or to a ground potential source; and a layer of chemical sensitive material overlying said conductive layer, said layer of chemical sensitive material being adapted to create an electrochemical voltage when exposed to selected chemical substances and to apply said electrochemical voltage at said conductive layer, said electrochemical voltage being referenced through said reference electrode to said diffusion regions.

3. Apparatus as defined in claim 2 wherein said conductive layer is comprised of an opaque material.

4. Apparatus as defined in claim 2 wherein said conductive layer is comprised of a material that is essentially chemically inert with respect to said electrical insulator material and said chemically sensitive material.

5. Apparatus as defined in claim 4 wherein said material of said conductive layer is selected from the group consisting of aluminum, gold, platinum, silver, tungsten, conductive polycrystalline silicon, and molybdenum.

6. Apparatus for measuring the concentration of chemical substances comprising:

a semiconductor substrate having a doping polarity;

a pair of spaced-apart diffusion regions located at the surface of said substrate material and having a doping polarity opposite that of said substrate material;

an electrical insulator material overlying at least a portion of said diffusion regions and the surface of the substrate material lying between the diffusion regions;

a conductive layer of material imbedded inside of said electrical insulator material so as to be completely surrounded thereby and positioned so as to be overlying, but not in electrical contact with, the surface area of said substrate material lying between said diffusion regions;

switch means for electrically connecting the conductive layer of material selectively to a voltage source or to a ground potential source; and chemical sensing means positioned above the conductive layer of material for generating an electrochemical voltage which is a function of the concentration of certain chemical substances to which said chemical sensitive means is exposed.

7. Apparatus as defined in claim 6 wherein said conductive layer is comprised of an opaque material.

8. Apparatus as defined in claim 6 wherein said imbedded conductive layer is comprised of a material that is essentially chemically inert with respect to said electrical insulator material.

9. Apparatus as defined in claim 8 wherein said material of the conductive layer is selected from the group consisting of aluminum, gold, platinum, silver, tungsten, conductive polycrystalline silicon, and molybdenum.

10. Apparatus for measuring the concentration of chemical substances comprising:

a semiconductor substrate having a doping polarity;

a pair of spaced-apart diffusion regions located at the surface of said substrate material and connected along the surface by a connecting layer region, said regions having a doping polarity opposite that of said substrate material;

a conductive Schottky barrier gate layer overlying at least a portion of said connecting layer region;

a reference electrode coupled in circuit relationship with said diffusion regions through a reference potential source;

switch means for electrically connecting the Schottky barrier gate layer selectively to a voltage source or to a ground potential source; and a layer of chemical sensitive material overlying said Schottky barrier gate layer, said chemical sensitive material being adapted to create an electrochemical voltage when exposed to selected chemical substance and to apply said electrochemical voltage at said Schottky barrier gate layer, said electrochemical voltage being referenced through said reference electrode to said diffusion regions.

11. Apparatus as in claim 10 wherein said Schottky barrier gate layer is a material selected from the group consisting of aluminum and platinum.

12. Apparatus as defined in claim 10 further including an electrical insulator material overlying said Schottky barrier gate layer.

13. Apparatus as defined in claim 12 wherein said chemical sensitive means comprises a layer of chemical sensitive material overlying that portion of said electrical insulator material that is above said Schottky barrier gate layer, said chemical sensitive material being adapted to create said electrochemical voltage when exposed to selected chemical substances and to apply a control voltage via an electric field created by said electrochemical voltage at said Schottky barrier gate layer, said voltages being referenced through said reference electrode to said diffusion regions.

14. A monolithic integrated circuit for measuring the concentration of chemical substances comprising:

a semiconductor substrate having a doping polarity;

a first pair of spaced-apart diffusion regions located at the surface of said substrate material and having a doping polarity opposite that of said substrate material;

a second pair of spaced-apart diffusion regions located at the surface of said substrate material and having a doping polarity opposite that of said substrate material;

a third pair of spaced-apart diffusion regions located at the surface of said substrate material and having a doping polarity opposite that of said substrate material;

means electrically connecting a first region of the second pair of diffusion regions to a first region of the third pair of diffusion regions;

electrical insulator material overlying at least a portion of said diffusion regions and the surface of the substrate material lying between said first, second and third pairs of diffusion regions;

a first conductive layer overlying that portion of said electrical insulator material that lies over the substrate surface area between said first pair of spaced-apart diffusion regions, said first conductive layer being in electrical contact with said connecting means;

a second conductive layer overlying that portion of said electrical insulator material that lies over the substrate surface area between said second pair of spaced-apart diffusion regions;

a third conductive layer overlying that portion of said electrical insulator material that lies over the substrate surface area between said third pair of spaced-apart diffusion regions;

a chemical sensitive element positioned above said first conductive layer, said chemically sensitive element being adapted to create an electrochemical potential when exposed to selected chemical substances; and a reference electrode connected in circuit relationship with said first pair of spaced-apart diffusion regions through a potential source such that a potential is created and added to said electrochemical potential generated in said chemically sensitive element, thereby creating a composite electric field that is felt at said first conductive layer, said composite electric field thus serving to affect the conductivity between said first pair of diffusion regions.

15. A method of measuring the concentration of chemical substances using three field-effect transistors (FETs), each having source, drain, and gate terminals, and a first of which further has a chemically sensitive element overlying its gate region, said method comprising:

(a) connecting the three FETs in circuit relationship as follows:

(1) electrically connecting the gate of the first FET to the source terminal of a second FET and the drain terminal of a third FET, (2) grounding the source terminals of the first and third FETs, (3) connecting an external potential source between ground and the drain terminal of the second FET, (4) connecting an external potential source between ground and the drain terminal of the first FET, and (5) connecting a current measuring device in series with the first FET so as to measure the amount of current that flows between the source and drain terminals thereof;

(b) exposing said chemically sensitive element of said first FET to a substance in which the concentration of chemical substances is to be measured;

(c) placing a reference electrode in contact with said substance whose concentration of chemical substances is to be measured, said reference electrode being connected to an external potential source that is referenced to ground;

(d) biasing the gate terminals of said second and third FETs so that they both act as switches, with the third FET being biased ON and the second FET being biased OFF, thereby applying a ground potential through the third FET to the gate terminal of the first FET;

(e) maintaining said third FET in the ON condition and said second FET in the OFF condition until a measurement is to be made, thereby protecting said first FET from static electric charge during manufacture, routine handling, and when not in use;

(f) biasing the gate terminals of said second and third FETs so that the third FET is OFF and the second FET is ON whenever the electrical characteristics of the first FET are to be measured, said biasing causing whatever reference potential is present at the drain terminal of said second FET as applied in step (a) (3) above to be directed through the second FET to the gate terminal of the first FET, said fixed gate potential thereby preventing any variations in the gate potential of the first FET that might otherwise occur due to the creation of an electrochemical potential by the chemically sensitive layer;

(g) biasing the gate terminals of said second and third FETs so that both FETs are OFF when a measurement of the concentration of chemical substances is to be made, thereby isolating the gate terminal of said first FET from all external potentials and allowing said electrochemical potential generated by said chemically sensitive element, and referenced to said first FET through the reference electrode mentioned in step (e), to vary the gate potential of the first FET in proportion to the concentration of selected chemical substances to which said chemically sensitive element is exposed, said variation affecting the conductivity between the source and drain terminals of the first FET; and (h) measuring the current that flows between the source and drain terminals of the first FET, said measure of current representing a measure of the concentration of chemical substances to which the first FET is exposed.

16. A method of measuring the concentration of chemical substances as defined in claim 15 wherein said first and second FETs are enhancement mode FETs and said third FET is a depletion mode FET.

17. A method of measuring the concentration of chemical substances as defined in claim 15 wherein said first, second, and third FETs are fabricated on the same semiconductor substrate, thereby forming a single monolithic integrated circuit that can be used for the measurement process.

* * * * *